United States Patent [19]

Haffer et al.

[11] Patent Number: 4,644,062

[45] Date of Patent: Feb. 17, 1987

[54] PROCESS FOR THE PRODUCTION OF β-CARBOLINES BY DEHYDROGENATION

[75] Inventors: Gregor Haffer; Helmut Börner; Andreas Huth, all of Berlin, Fed. Rep. of Germany

[73] Assignee: Schering Aktiengesellschaft, Berlin and Bergkamen, Fed. Rep. of Germany

[21] Appl. No.: 825,718

[22] Filed: Feb. 3, 1986

[30] Foreign Application Priority Data

Feb. 4, 1985 [DE] Fed. Rep. of Germany ....... 3504045

[51] Int. Cl.$^4$ ............................................. C07D 471/04
[52] U.S. Cl. ........................................ 546/85; 546/86; 546/87
[58] Field of Search ...................... 546/85, 86, 87

[56] References Cited

U.S. PATENT DOCUMENTS 4,321,402  3/1982  Ryu et al. ............................. 260/453
4,596,808  6/1986  Braestrup et al. ..................... 546/86

OTHER PUBLICATIONS

Bravindranath et al., Reaction of d-Limonene with t-Butyl Hypochlorite.

Primary Examiner—Henry R. Jiles
Assistant Examiner—J. Richter
Attorney, Agent, or Firm—Millen & White

[57] ABSTRACT

β-carbolines of formula I

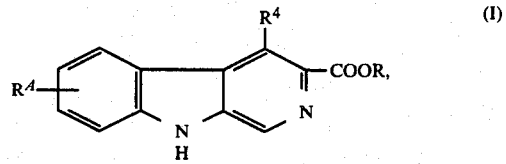

wherein
R = $C_{1-5}$ alkyl
$R^4$ = H, $C_{1-5}$ alkyl or —$(CH_2)_n$—OR with n = 1 or 2 and
$R^A$ = H, R, $(CHR)_n$—OR, $OCH_2Ph$, OPh, OPh(Cl,Br-),OR,$OCH_2Ph$(Cl,Br) NRR, Cl or Br,
wherein n and R have the above meanings and there are one or two $R^A$'s are prepared, by dehydrogenation at reaction temperatures below ambient temperature in an inert solvent with tert-butyl hypochlorite and a tertiary amine.

9 Claims, No Drawings

PROCESS FOR THE PRODUCTION OF β-CARBOLINES BY DEHYDROGENATION

BACKGROUND OF THE INVENTION

The invention relates to a new process for the production of β-carbolines from the corresponding 1,2,3,4-tetrahydro-β-carbolines by dehydro-genation.

Processes for the production of β-carbolines from 1,2,3,4-tetrahydro-β-carbolines have been known for a long time (e.g., see GB PS No. 975,835). According to the latter, dehydrogenation is carried out at an elevated temperature in the 140°–150° C. range in a suitable solvent such as dimethylformamide in the presence of selenium, sulfur or chloranil. Sulfur/dimethylsulfoxide can also be successfully used (Heterocycles, 1983 (20), 1293). However, these methods have the disadvantage that the yields leave much to be desired due to a relatively drastic treatment of the starting material and the subsequent separation of by-products.

SUMMARY OF THE INVENTION

It is an object of this invention to provide a process overcoming or ameliorating these disadvantages.

Upon further study of the specification and appended claims, further objects and advantages of this invention will become apparent to those skilled in the art.

These objects have been achieved according to the invention by performing the dehydrogenation at a reaction temperature below ambient temperature in an inert solvent with tert-butyl hypochlorite in the presence of a tertiary base.

Thus, this invention relates to a process for the production of β-carbolines of formula I

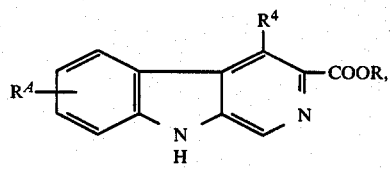

wherein
R = $C_{1-5}$ alkyl,
$R^4$ = H, $C_{1-5}$ alkyl or —(CH$_2$)$_n$—OR with n=1 or 2 and
$R^A$ = H, R. (CHR)$_n$—OR, OCH$_2$Ph, OPh, OPh(Cl, Br), OR, OCH$_2$Ph(Cl, Br) NRR, Cl or Br, wherein n and R have the meanings indicated above and the substituent $R^A$ may occur once or twice, from the corresponding tetrahydrocarbolines of formula II

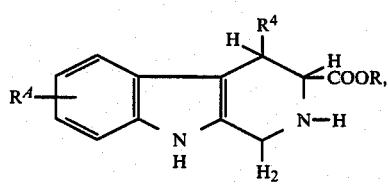

wherein
$R^A$, $R^4$ and R have the meanings indicated above, comprising dehydrogenating the latter at reaction temperatures below ambient temperature in an inert solvent with tert-butyl hypochlorite and a tertiary base.

DETAILED DISCUSSION

Reactions of nitrogen compounds with electrophilic reagents such as tertbutyl hypochlorite, are known, e.g., N-chlorination (J. S. Chalsty and S. S. Israelstam, Chem. and Ind. 1954, 1452; H. E. Baumgarten and J. M. Petersen, Org. Syn. 1973, Coll. Vol. 5, 909 and J. Vit and S. J. Barer, Synth. Comm. 1976, 1), as well as C-chlorination in the electrophilic substitution of indole compounds in the 3-position (R. J. Sundberg, The Chemistry of Indoles in Organic Chemistry 18, p. 10,15 Academic Press, New York and London, 1970 and A. J. Gaskell, H.-E. Radunz and E. Winterfeldt, Tetrahedron 1970 (26), 5353). Thus, it is surprising that the reaction according to the invention even with an excess of tert-butyl hypochlorite does not result in chlorination on the aromatic A ring of the β-carboline molecule. The process according to the invention especially has the advantage that higher yields of the desired β-carboline are attained, e.g., in the range of 50–80 mole %. Furthermore, it has the advantage that only mild reaction conditions need be used and the isolation of the reaction product is simpler and more ecologically compatible than according to known processes requiring distilling off of a high-boiling solvent, separation of by-products by chromatography, removal of polymeric sulfur, disposal of waste products such as dimethylsulfoxide and dimethylsulfide, etc.

Alkyl radicals R of up to 5 C atoms can be both straight-chained and branched. Methyl, ethyl, n-propyl, isopropyl, n-butyl and tert-butyl are typical examples, along with other butyls and the pentyls. $R^A$ can also be in any position or combination thereof on the A ring, preferably in the 5-, 6- or 7-position. In OPh (Cl, Br) and OCH$_2$Ph (Cl, Br) the Cl and/or Br substituents (I-2) can be on any position, preferably one substituent on 3- or 4-position, two substituents on 2,4-position.

All of the compounds that can be produced by the process according to the invention are either themselves biologically effective or are valuable intermediate products for the production of biologically effective β-carbolines, such as, e.g., 5-benzyloxy-4-methoxymethyl-β-carboline-3-carboxylic acid ethyl ester (G. Neef et al., Heterocycles 1983 (20), 1295) or of 4-methoxy-5-benzyloxy-3-[5-(3-ethyl-1,2,4-oxadiazol)-yl]carboline by saponification of the free 3-carboxylic acid, reaction with thionyl diimidazole and propionamidoxime and condensation under heat to the oxadiazolyl ring system in 3-position. See EP No. 00 54 507 U.S. Pat. No. 4,435,403, U.S. Pat. No. 4,371,536 and EP No. 00 30 254, which references are incorporated by reference herein.

Non-limiting examples of suitable inert solvents include, e.g., aromatic hydrocarbons such as benzene, toluene, xylene, chlorinated hydrocarbons such as methylene chloride, chloroform, carbon tetrachloride and 1,2-dichloroethane and ethers such as diethyl ether, tetrahydrofuran, dioxane, diisopropyl ether and tert-butylmethyl ether. 2–15 liter solvents are added pro 1 mol tetrahydro-β-carboline.

The tert-butyl hypochlorite is generally added in a quantity of 2.0 to 3.5, preferably about 3.0 mole-equivalents relative to the amount of tetrahydro-β-carboline used.

Non-limiting examples of suitable tertiary bases include amines, e.g., triethylamine, tributylamine, ethyldiisopropylamine in a molar ratio tert.base:tert. butyl hypochlorite = 1.5–2.5:1, ethyldiisopropylamine, 1,5- diazabicyclo-[4.3.0]-non-5-ene (DBN), 1,8-diazabicyclo-[5.4.0]-undec-7-ene (DBU) or dimethylaminopyridine (DMAP); triethylamine is preferred.

The reaction temperature for the dehydrogenation according to the invention is below ambient temperature (i.e., less than about 20° or 25° C.); about, −70° C. being a typical lower limit. The −15° to −5° C. range is preferred. Working under a protective gas, such as under a nitrogen atmosphere, is advantageous. The course of the reaction can be conventionally tracked by thin-layer chromatography and typically is ended after 2 to 6 hours conventionally depending on the starting material and the other conditions.

The dehydrogenation of tetrahydro-β-carbolines according to the invention is a *two-step reaction:* halogenation and dehydrohalogenation. The reaction advantageously is carried out so that the starting material is dissolved in the solvent, this solution is cooled as described above, the tertiary base is added and the tert.-butyl hypochlorite, optionally diluted in an inert solvent, is slowly added to this solution in order to chlorinate the tetrahydro-β-carboline. After 15-30 minutes, further addition of tertiary base, the reaction temperature is allowed to rise to ambient temperature, preferably with stirring to complete dehydrohalogenation leading to β-carbolines for 2-6 hours.

The reaction mixture is worked up in the usual manner by filtration, distillation, crystallization and/or chromatography.

The starting materials are all known and or readily preparable from known materials using conventional processes, e.g., as described in the examples.

EXAMPLE 1

10 mmol of 5-benzyloxy-4-methoxymethyl-1,2,3,4-tetrahydro-β-carboline-3-carboxylic acid ethyl ester is dissolved in 45 ml of methylene chloride. The solution is cooled to −15° C. and 4.6 ml of triethylamine is added Then a solution of 3.6 ml of tert-butyl hypochlorite in 45 ml of methylene chloride is added within about 10 minutes and stirred for 5 minutes more. After further addition of 3.8 ml of triethylamine, heating to ambient temperature and stirring at this temperature for 4 hours takes place. The solvent is distilled off in vacuum (bath temperature +30° C.) and condensed to dryness at +60° C. bath temperature. The residue is taken up in methylene chloride, filtered over silica gel, rewashed with methylene chloride, the product is eluted with ethyl acetate, the eluate is condensed and washed with ice water. The precipitate is filtered off and wahsed with ice-cold ethyl acetate. 2.93 g of 5-benzyloxy-4-methoxymethyl-β-carboline-3-carboxylic acid ethyl ester (80.5% of theory) with melting point 190.0° C. is obtained.

Production of the starting material:

10.8 g of glyoxylic acid monohydrate dissolved in 120 ml of water is added under vigorous stirring to a solution of 37.6 g of 3-(4-benzyloxyindol-3-yl)-2-amino-5-oxa-hexanoic acid ethyl ester (98.9 mmol) in 250 ml ethyl acetate. The solution is adjusted to pH 4 with 15 ml of 10% aqueous potassium carbonate solution, stirred for 14 hours at ambient temperature, the light yellow crystalline precipitate is filtered off, rewashed with a little ethyl acetate and dried. The separated organic phase of the filtrate is dried over sodium sulfate, and condensed in vacuum, whereby an orange-yellow oil is obtained.

Yield: 17.5 g of crystals with a melting point of 120°-140° C. and 19.0 g of oily product (84.7% of theory).

10 g of crystalline 5-benzyloxy-3-ethoxycarbonyl-4-methoxymethyl-1,2,3,4-tetrahydro-β-carboline-1-carboxylic acid is heated to boiling for 1 hour in 200 ml of xylene and the xylene is distilled off to dryness in vacuum. (decarboxylation) After crystallization from ethyl acetate, the residue yields 8.83 g of 5-benzyloxy-4-methoxymethyl-1,2,3,4-tetrahydro-β-carboline-3-carboxylic acid ethyl ester with a melting point of 170°-171° C. (98.2% of theory).

EXAMPLE 2

Analogously to example 1, whereby, however, in place of triethylamine, 1,8-diazabicyclo-[5,4,0]undec-7-ene is used as base, 4-ethyl-6,7-dimethoxy-β-carboline-3-carboxylic acid ethyl ester is obtained from 1 mmol of 4-ethyl-6,7-dimethoxy-1,2,3,4-tetrahydro-β-carboline-3-carboxylic acid ethyl ester with a melting point of 229°-231° C. in 68% yield.

Production of the starting material:

3 mmol of 2-amino-3-(5,6-dimethoxyindol-3-yl)pentanoic acide ethyl ester is dissolved under nitrogen atmosphere in 8 ml of ethyl acetate, and 4 ml of water and 357 mg of glyoxylic acid monohydrate is added to this solution. The solution is adjusted to pH 4 with 0.55 ml of 10% aqueous potassium carbonate solution, stirred for 14 hours at ambient temperture, cooled to 5°-10° C., filtered, the residue is washed with ice-cold ethyl acetate, the filtrate is condensed in vacuum and dried with sodium sulfate. The residue is recrystallized from ethyl acetate and dried. 894 mg (79.2% of theory) of 4-ethyl-6,7-dimethoxy-1,2,3,4-tetrahydro-β-carboline-1,3-dicarboxylic acid-3-monoethyl ester is obtained with a melting point of 143°-147° C., which is refluxed for 2 hours in 5 ml of toluene under a nitrogen atmosphere. The toluene is distilled off, whereby the residue is crystallized from ethyl acetate as described in Example 1.

EXAMPLE 3

Analogously to Example 1, whereby, however, instead of at −15° C., the reaction is performed at +5° C., 126 mg of 6-benzyloxy-4-methyl-β-carboline-3-carboxylic acid ethyl ester with a melting point of 231°-233° C. is obtained from 1 mmol of 6-benzyloxy-4-methyl-1,2,3,4-tetrahydro-β-carboline-3-carboxylic acid ethyl ester (mp, 152°-155° C.) after recrystallization from ethyl acetate.

EXAMPLE 4

Analogously to Example 1 but with double the quantity of tert-butyl hypochlorite, 214 mg of 6-benzyloxy-4-ethyl-β-carboline-3-carboxylic acid ethyl ester with a melting point of 176°-177° C. is obtained from 1 mmol of 6-benzyloxy-4-ethyl-1,2,3,4-tetrahydro-β-carboline-3-carboxylic acid ethyl ester (mp, 166°-168° C.) after recrystallization from ethyl acetate.

EXAMPLE 5

Analogously to Example 1, however without isolating the decarboxylated intermediate stage (decarboxylation and dehydrogenation as a *one-pot reaction*), 215 mg of 5-(3-chlorobenzyloxy)-4-methoxymethyl-β-carboline-3-carboxylic acid ethyl ester with a melting point of 178°-179° C. is obtained from 1 mmol of 5-(3-chlorobenzyloxy)-4-methoxymethyl-1,2,3,4-tetrahydro- β-carboline-1,3-dicarboxylic acid 3-monoethyl ester after recrystallization from ethyl acetate.

EXAMPLE 6

The following compounds of formula I are produced under the reaction conditions of Example 1:

| | R | R⁴ | R$^A$ | mp/(°C.) | Yield (% of Theory) |
|---|---|---|---|---|---|
| (a) | C₂H₅ | H | 5-CH₃ | 257 | 60.2 |
| (b) | C₂H₅ | CH₃ | 5-CH(C₂H₅)(OC₂H₅) | 185–186 | 48.3 |
| (c) | C₂H₅ | CH₂—OCH₃ | 5-CH(CH₃)(OC₂H₅) | 144–148 | 33.1 |
| (d) | C₂H₅ | CH₂—OCH₃ | H | 116–118 | 72.0 |
| (e) | C₂H₅ | CH₃ | 5-O—CH(CH₃)₂ | 166–168 | 74.6 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of a β-carboline of the general formula

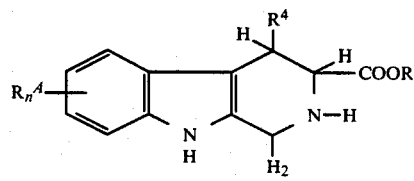

wherein
R⁴ is H, C$_{1-5}$-alkyl or —(CH₂)$_n$—OR each R$^A$ independently is H, R, (CHR)$_n$—OR, OCH₂Ph, OPh, OPh and OCH₂Ph substituted by Cl, Br or both Cl and Br, OR, NRR, Cl or Br,
each R independently is C$_{1-5}$ alkyl,
each n independently is 1 or 2
comprising dehydrogenating the corresponding tetrahydrocarboline of the formula

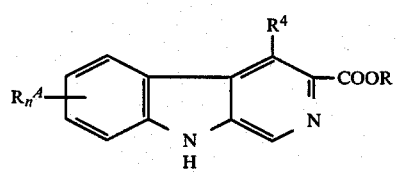

wherein
R$^A$, R⁴, n and R are as defined above,
at a reaction temperature below ambient temperature, in a reaction compatible inert solvent, with amounts of tert-butyl hypochlorite and a tertiary amine effective to produce said β-carboline.

2. A process of claim 1 wherein the reaction temperature is −70° C. to below ambient temperature.

3. A process of claim 1 wherein the reaction temperature is about −15° to −5° C.

4. A process of claim 1 comprising, after rection at said temperatures below ambient for 15–30 minutes, conducting the reaction at about ambient temperature for 2–6 hours.

5. A process of claim 1 wherein the inert solvent is an aromatic hydrocarbon, a chlorinated hydrocarbon, or an ether.

6. A process of claim 5 wherien the inert solvent is benzene, toluene, xylene, methylene chloride, chloroform, carbon tetrachloride, 1,2-dichloroethane, diethyl ether, tetrahydrofuran, dioxane, diisopropyl ether, or tert-butylmethyl ether.

7. A process of claim 1 wherein the amount of tert-butyl hypochlorite is 2.0 to 3.5 mole equivalents relative to the tetrahydro-β-carboline.

8. A process of claim 1 wherein the tertiary base is triethylamine, tributylamine, ethyldiisopropylamine, 1,5-diazabicyclo-[4.3.0]-non-5-ene, 1,8-diazabicyclo-[5.4.0]-undec-7-ene or dimethylaminopyridine.

9. A process of claim 1 carried out under a protective gas atmosphere.

* * * * *